United States Patent [19]
Spears

[11] Patent Number: 5,599,296
[45] Date of Patent: Feb. 4, 1997

[54] APPARATUS AND METHOD OF DELIVERY OF GAS-SUPERSATURATED LIQUIDS

[75] Inventor: James R. Spears, Bloomfield Hills, Mich.

[73] Assignee: Wayne State University, Detroit, Mich.

[21] Appl. No.: 353,137

[22] Filed: Dec. 9, 1994

Related U.S. Application Data

[63] Continuation-in-part of Ser. No. 273,652, Jul. 12, 1994, which is a continuation-in-part of Ser. No. 152,589, Nov. 15, 1993, Pat. No. 5,407,426, which is a continuation-in-part of Ser. No. 818,045, Jan. 8, 1992, Pat. No. 5,261,875, which is a continuation of Ser. No. 655,078, Feb. 14, 1991, Pat. No. 5,086,620.

[51] Int. Cl.$^6$ .................................................. A61M 37/00
[52] U.S. Cl. ............................ 604/26; 604/24; 604/21; 604/264
[58] Field of Search ................................ 128/657, 658, 128/772; 604/23–26, 93, 264, 280, 282, 21, 53

[56] References Cited

U.S. PATENT DOCUMENTS

| | | |
|---|---|---|
| 2,975,606 | 3/1961 | Karwat . |
| 3,459,565 | 8/1969 | Jones et al. . |
| 3,498,286 | 3/1970 | Polanyi .................................. 604/21 |
| 3,721,231 | 3/1973 | Hubert ................................... 128/658 |
| 3,963,503 | 6/1976 | Mackenzie . |
| 3,972,721 | 8/1976 | Hammel et al. . |
| 4,104,074 | 8/1978 | Resteker . |
| 4,122,858 | 10/1978 | Schiff . |
| 4,175,545 | 11/1979 | Termanini .............................. 604/21 |
| 4,285,977 | 8/1981 | Yezek et al. . |
| 4,303,432 | 12/1981 | Torobin . |
| 4,323,420 | 4/1982 | Masnari et al. . |
| 4,332,907 | 6/1982 | Viehl . |
| 4,332,908 | 6/1982 | Viehl . |

(List continued on next page.)

OTHER PUBLICATIONS

"Use of Hyperbaric Oxygen as Oxygen Source in Extracorporeal Oxygenation of Blood", C. Boe, et al; Physiological and Clinical Aspects of Oxygenator Design, ed. by Dawids and Engell; publ. by Elsevier/North–Holland Biomedical Press, Luxembourg, 1976.

"Cavitation in Gas–Supersaturated Solutions", Edvard A. Hemmingsen; Journal of Applied Physics, vol. 46, No. 1, Jan. 1976.

"Supersaturated Fluorocarbon as an Oxygen Source", Pieter Stroev, et al; Physiological and Clinical Aspects of Oxygenator Design, ed. by Dawids and Engell; publ. by Elsevier/ North–Holland Biomedical Press, Luxembourg, 1976.

*Primary Examiner*—Randall L. Green
*Assistant Examiner*—Chalin Smith
*Attorney, Agent, or Firm*—Brooks & Kushman PC

[57] ABSTRACT

An apparatus 10 for delivery of a gas, such as oxygen, solution into an environment (such as a coronary artery). The apparatus includes a high pressure tubular housing 12 defining a lumen 14 therewithin. A plurality of axially disposed concentric tubes 16 are supported within the lumen 14. Each defines an annular space 18 between adjacent tubes. One or more supports 20 extend radially inwardly from the tubular housing 12. The supports are connected to the concentric tubes 16 to prevent radially or axially migration thereof during high pressure infusion of the oxygen supersaturated physiologic solution. The method includes the steps of compressing a carrier to form a compressed carrier for transporting the gas to eliminate gas nuclei before exposure of the carrier to the gas; exposing the compressed carrier to the gas under pressure to form a gas-saturated compressed carrier; transporting the gas-saturated compressed carrier to the delivery system; and infusing the gas supersaturated compressed carrier from the delivery system at an exit port to the environment without associated bubble formation and cavitation proximate the exit port so that the gas is transported to the site within the environment in solution with the carrier in a supersaturated state, the gas being liberated therefrom remote from the exit port upon arrival at the site within the environment.

14 Claims, 3 Drawing Sheets

U.S. PATENT DOCUMENTS

| | | | |
|---|---|---|---|
| 4,347,326 | 8/1982 | Iwami et al. . | |
| 4,385,635 | 5/1983 | Ruiz . | |
| 4,445,896 | 5/1984 | Gianturco . | |
| 4,450,841 | 5/1984 | Osterholm . | |
| 4,572,203 | 2/1986 | Feinstein . | |
| 4,573,476 | 3/1986 | Ruiz . | |
| 4,610,661 | 9/1986 | Possis et al. . | |
| 4,661,094 | 4/1987 | Simpson | 604/53 |
| 4,674,480 | 6/1987 | Lemelson . | |
| 4,748,984 | 6/1988 | Patel | 128/658 |
| 4,808,163 | 2/1989 | Laub | 604/53 |
| 4,834,719 | 5/1989 | Arenas . | |
| 4,850,958 | 7/1989 | Berry | 604/53 |
| 4,877,031 | 10/1989 | Conway et al. . | |
| 4,930,319 | 6/1990 | Bee et al. . | |
| 4,963,130 | 10/1990 | Osterholm . | |
| 4,969,878 | 11/1990 | Schmidt et al. . | |
| 5,021,044 | 6/1991 | Sharkawy . | |
| 5,037,403 | 8/1991 | Garcia . | |
| 5,044,164 | 9/1991 | Bee . | |
| 5,072,739 | 12/1991 | John . | |
| 5,084,011 | 1/1992 | Grady | 604/24 |
| 5,086,620 | 2/1992 | Spears . | |
| 5,114,423 | 5/1992 | Kasprzyk et al. . | |
| 5,116,317 | 5/1992 | Carson, Jr. et al. . | |
| 5,137,513 | 8/1992 | McInnes et al. . | |
| 5,158,540 | 10/1992 | Wijay et al. . | |
| 5,180,364 | 1/1993 | Ginsburg . | |
| 5,195,971 | 3/1993 | Sirhan . | |
| 5,211,637 | 5/1993 | Goto et al. . | |
| 5,226,888 | 7/1993 | Arney . | |
| 5,252,159 | 10/1993 | Arney . | |
| 5,261,875 | 11/1993 | Spears . | |
| 5,273,052 | 12/1993 | Krans et al. . | |
| 5,279,562 | 1/1994 | Sirhan et al. . | |
| 5,322,508 | 6/1994 | Viera . | |
| 5,334,142 | 8/1994 | Paradis . | |
| 5,356,388 | 10/1994 | Sepetka | 604/282 |
| 5,370,640 | 12/1994 | Kolff | 604/21 |
| 5,376,069 | 12/1994 | Hattler | 604/26 |
| 5,383,853 | 1/1995 | Jung et al. . | |
| 5,413,558 | 5/1995 | Paradis . | |
| 5,425,703 | 6/1995 | Feiring | 604/21 |
| 5,437,633 | 8/1995 | Manning . | |
| 5,498,251 | 3/1996 | Dalton . | |

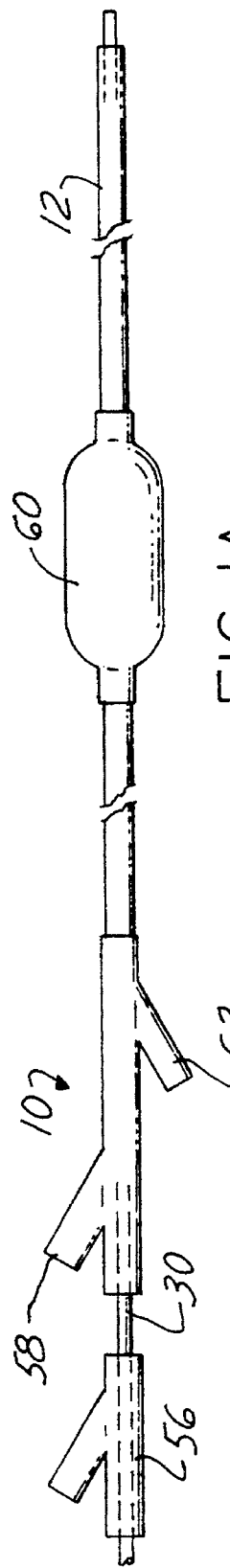
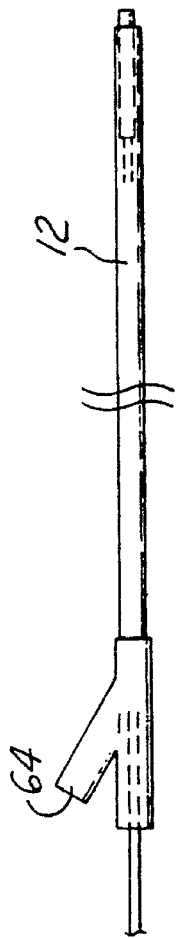
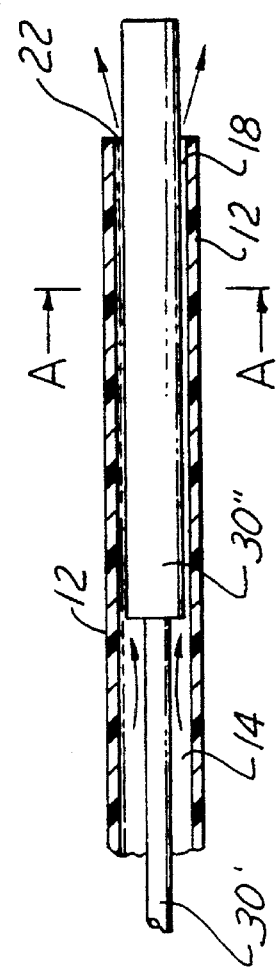

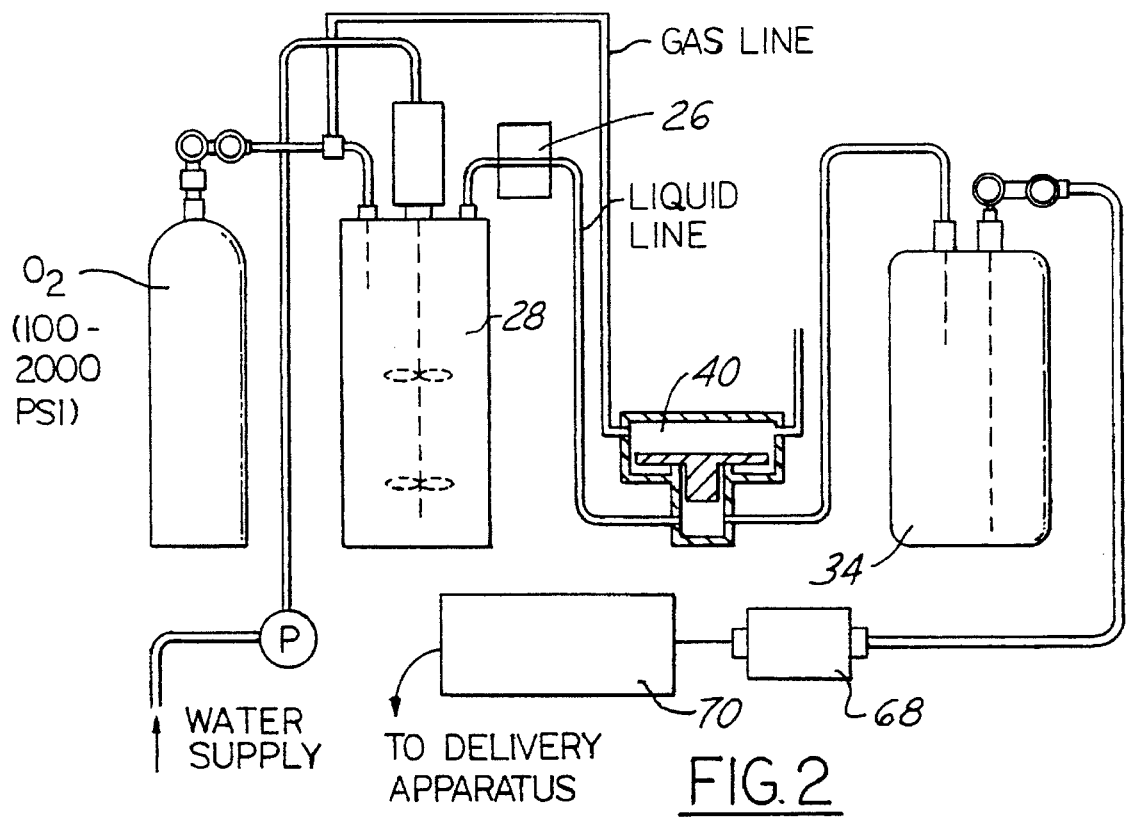
FIG. 2
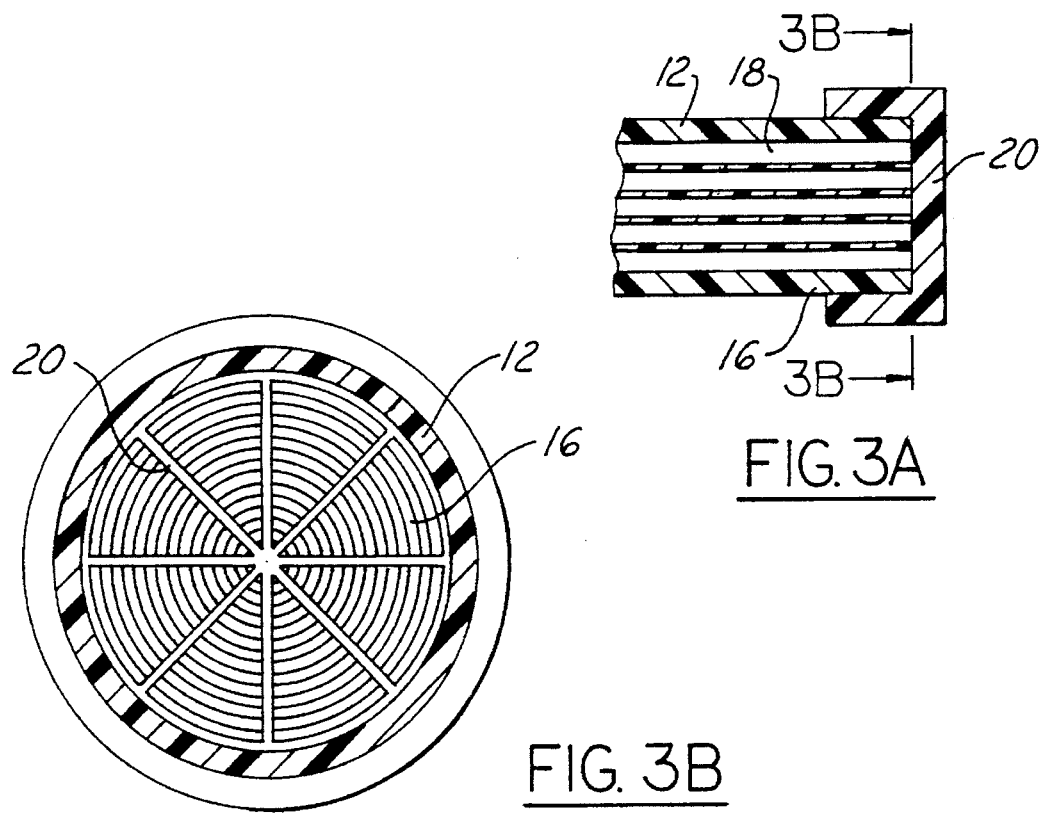
FIG. 3A
FIG. 3B

APPARATUS AND METHOD OF DELIVERY OF GAS-SUPERSATURATED LIQUIDS

CROSS REFERENCE TO RELATED APPLICATION

This application is a continuation-in-part of application Ser. No. 273,652, filed Jul. 12, 1994, which is a continuation-in-part of application Ser. No. 152,589, filed Nov. 15, 1993 (now U.S. Pat. No. 5,407,426), which is a continuation-in-part of application Ser. No. 818,045, filed Jan. 8, 1992 (now U.S. Pat. No. 5,261,875), which is a continuation of application Ser. No. 655,078, filed Feb. 14, 1991 (now U.S. Pat. No. 5,086,620). Each of these disclosures is incorporated by reference herein.

TECHNICAL FIELD

The invention relates to an apparatus and method of delivery of gas-supersaturated liquids into a variety of environments in a manner which stabilizes the dissolved gas, so that cavitation nucleation does not occur at the exit port of the delivery system. More specifically, the invention relates to an apparatus and method of delivery of oxygen-supersaturated liquids into the blood stream.

BACKGROUND ART

In previous disclosures, I described methods for achieving the goal of delivering gas-supersaturated liquids into a variety of environments in a manner which stabilizes the dissolved gas, so that cavitation nucleation does not occur at the exit port of the delivery system.

In the medical environment, regional tissue hypoxia, despite normal respiratory function, is a pathologic substrate responsible for many serious conditions. Hyperbaric oxygen therapy may provide clinical benefit in the treatment of regional ischemia associated with a wide variety of medical problems, but it is limited to 90 minutes/day at 2.5 bar because of the potential for pulmonary oxygen toxicity. Intravenously injected perfluorochemical emulsions may increase the oxygen content of plasma, but do not increase the partial pressure of oxygen in arterial blood. Attempts to infuse dilute solutions of hydrogen peroxide into blood result in uncontrolled foaming during its decomposition by tissue catalase.

In the setting of arterial occlusion, restoration of blood flow may not be possible or may result in tissue hemorrhage and edema, which increases the distance for oxygen diffusion. For other clinical settings, such as radiation-resistant hypoxic neoplasms, radiation-injured tissue adjacent to neoplasms, and a variety of non-healing wounds or infections, arterial occlusion is not a consideration. At present, no interventional technique is available for treatment of regional tissue hypoxia when local blood flow cannot be normalized.

Myocardial ischemia occurs transiently in the majority of patients subjected to coronary angioplasty procedures, including both balloon angioplasty and newer modalities such as directional atherectomy, rotational atherectomy, and stent placement. The duration of balloon inflation is usually determined by the severity of myocardial ischemia, rather than by the operator's estimate of the potential utility of longer balloon inflations. Typically, evidence of severe ischemia, commonly chest pain and ECG changes and occasionally hemodynamic or electrical instability, requires that the operator deflate the balloon in approximately 60 to 120 seconds. For anatomically difficult lesions, such as type B and C lesions, which presently comprise approximately ½ of all lesions treated with angioplasty, longer periods of balloon inflation are frequently desirable for the first balloon inflation.

In addition, following the initial brief inflation in many lesions, including morphologically uncomplicated ones, a longer balloon inflation is frequency desirable because of a suboptimal luminal result. Although luminal morphology following stent deployment is usually satisfactory, attempts to advance a stent crimped on a deflated balloon into a tortuous vessel may also be associated with a prolonged period of ischemia.

Autoperfusion balloon catheters permit much longer periods of balloon inflation in most patients in whom this approach is used. However, blood flow through these catheters is inadequate when the systemic arterial pressure is low and may be inadequate in some patients despite a normal blood pressure. The deflated profile of autoperfusion balloon catheters, particularly at the distal balloon end, is relatively bulky compared to standard balloon catheters. As additional drawbacks, it is usually necessary to withdraw the guidewire from the autoperfusion balloon to facilitate perfusion, and the catheters are relatively expensive. Despite these problems, 17% of all coronary balloon catheters used in the U.S. today are autoperfusion catheters. As autoperfusion catheters have been technically refined, such as the development of the monorail system, their utilization has increased.

Occasional instances of myocardial ischemia occur during angioplasty despite achievement of an adequate luminal result. For example, multiple emboli are produced during rotational atherectomy, and depression of myocardial performance may be reduced for many hours as a result. Balloon angioplasty is successful in restoration of an adequate lumen in the vast majority of patients presented with an acute myocardial infarction. But a "no reflow" phenomenon occasionally occurs, very likely as a result of intramyocardial hemorrhage, edema, and perhaps neutrophil entrapment of the microvasculature.

Hemmingsen and co-workers two decades ago demonstrated that water, under static conditions, can be supersaturated with a variety of gases, including oxygen at a partial pressure as great as 140 bar, without bubble formation upon release to 1 bar. Application of high hydrostatic pressure is the most effective means for elimination of cavitation nuclei. Alternative means such as filtration, prolonged standing, boiling, or application of a vacuum are less effective for this purpose. An important mechanism responsible for the high tensile strength of water, in the absence of cavitation nuclei, is the fact that the formation or growth of a bubble at the molecular level (e.g., on the order of 50 Å diameter) requires large pressures, in theory>1 kbar, to overcome the effect of the surface tension of water (Laplace relationship).

The studies of Hemmingsen and prior investigators of the ability to supersaturate water with a gas, without cavitation formation upon release to 1 bar, have been performed under static conditions. Mechanical disturbance of the metastable fluid was noted by previous workers to result in bubble evolution. It was probably assumed that any attempt to eject the fluid into a 1 bar environment would be accompanied by a similar problem. What is now needed is a way to eject gas-supersaturated aqueous solutions from a high pressure vessel into a 1 bar environment without associated bubble formation in the effluent.

SUMMARY OF THE INVENTION

Described herein are an apparatus and a method for infusion of gas-saturated solutions into an environment without cavitation inception in the effluent.

The apparatus includes a high pressure tubular housing within which concentric tubes are axially disposed. Each defines an annular space therebetween through which the gas-saturated liquid may pass.

The method of delivering gas-supersaturated liquids from a source of gas into a site within an environment having a low concentration of the gas comprises:

exposing a carrier to a compressed form of the gas to form a gas-saturated pressurized carrier;

compressing the gas-saturated pressurized carrier to form a compressed carrier for transporting the gas to eliminate gas nuclei from a delivery system;

transporting the gas-saturated compressed carrier to the delivery system at a pressure (P); and infusing the gas-saturated compressed carrier from the delivery system through an exit port to the environment at a pressure (p), where (P) exceeds (p), without associated bubble formation and cavitation proximate the exit port so that the gas is transported to the site in solution with the carrier in a supersaturated state.

When oxygen-supersaturated physiologic solutions (OSPS) are infused into arterial blood, the inherent tensile strength of nuclei-free water and blood permits achievement of oxygen tensions similar to those attained in hyperbaric oxygen chambers. A variety of medical conditions may benefit from intra-arterial infusion of OSPS, including myocardial ischemia during angioplasty, acute myocardial infarction, cerebrovascular accidents and hypoxic neoplasms which are resistant to radiation therapy. Oxygen concentrations as high as 4 cc $O_2$ (STP)/g, a concentration which exceeds that of arterial blood (0.2 cc $O_2$/g) by more than an order of magnitude, can be infused into aqueous media, including blood, without cavitation inception in the effluent. The known, inherent tensile strength of water, in the absence of cavitation nuclei (microscopic gas cavities associated with motes or surface imperfections and microscopic bubbles), is in part responsible for this observation.

Other applications requiring high flow rates of water include wastewater treatment and aeration of lakes, ponds, and the like. For such applications, the gas provided in the high flow rate effluent would usually be air at a high partial pressure, although oxygen alone could be used at a higher cost.

The above objects and other objects, features, and advantages of the present invention are readily apparent from the following detailed description of the best mode for carrying out the invention when taken in connection with the accompanying drawings.

BRIEF DESCRIPTION OF THE DRAWINGS

FIG. 1A is a schematic of an angioplasty apparatus including the delivery system of the present invention;

FIG. 1B is an enlarged portion of FIG. 1A;

FIG. 1C is an enlarged view of a portion of FIG. 1B;

FIG. 1D is a radial cross-sectional view of the embodiment of FIG. 1C taken along the line A—A of FIG. 1C;

FIG. 1E is a radial cross-sectional view of an alternate embodiment thereof;

FIG. 2 depicts a clinical saturated oxygen solution delivery system;

FIG. 3A is an axial sectional view of a concentric capillary array which forms an embodiment of the delivery system of the present invention;

FIG. 3B is a radial cross-sectional view taken along the line B—B thereof; and

BEST MODE(S) FOR CARRYING OUT THE INVENTION

Figure 4:
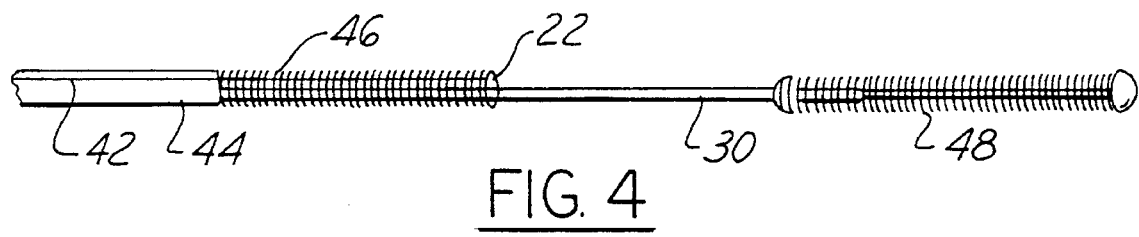
FIG. 4 depicts a distal end of an oxygen-saturated physiological solution perfusion guidewire.

The invention covers an apparatus and a method of delivering gas-supersaturated liquids from a source of gas into a site within an environment having a low concentration of the gas.

Turning to FIGS. 1 and 3, the apparatus 10 includes a high pressure tubular housing 12 defining a lumen 14 therewithin. A plurality of axially disposed concentric tubes 16 are supported within the lumen 14. Each defines an annular space 18 between adjacent tubes. Extending radially inwardly from the tubular housing 12 are one or more supports 20. Each support 20 is connected to the concentric tubes 16 to prevent radial or axial migration thereof during high pressure infusion of the oxygen-saturated physiologic solution.

To enable the oxygen-saturated physiologic solution to be delivered to the site without associated bubble formation and cavitation proximate the exit port 22, it has been found helpful to eliminate gas nuclei by "pre-loading" a charge of oxygen-saturated physiological solution within the lumen 14 and one or more of the annular spaces 18. The charge is characterized by a fluid continuum (i.e., no gas bubbles) of uniform density upon emergence from the exit port 22.

The method steps of the present invention comprise:

exposing a carrier to a compressed form of the gas to form a gas-saturated pressurized carrier;

compressing the gas-saturated pressurized carrier to form a compressed carrier for transporting the gas and to eliminate gas nuclei from a delivery system;

transporting the gas-saturated compressed carrier to the delivery system at a pressure (P); and infusing the gas-saturated compressed carrier from the delivery system through an exit port to the environment at a pressure (p), where (P) exceeds (p), without associated bubble formation and cavitation proximate the exit port so that the gas is transported to the site in solution with the carrier in a supersaturated state.

Preferably, the step of exposing the compressed carrier to the gas under pressure comprises the step of providing a membrane oxygenator 26 (FIG. 2). Alternatively, that step may comprise the step of providing a rapid mixer 28, or both a membrane oxygenator 26 and a rapid mixer 28.

I have found that the use of a space created by placement of a wire 30 (FIG. 1D) in a polymeric tube 12 or a polymeric tube within another such tube, will stabilize gas-supersaturated liquids at the distal end of the delivery system, if the space 18 between the wire and tube or the two tubes is appropriately small.

In FIG. 1A, there is depicted an exemplary environment within which the invention may be used. In the angioplasty catheter system, there is depicted a Y-adaptor 56 through which a guidewire 30 passes. A flushing port 58 permits a central channel or lumen 14 to be irrigated with a flushing solution. To permit inflation of the angioplasty balloon 60, a balloon inflation port 62 is provided. In FIG. 1B, the reference numeral 64 indicates the point of supersaturated oxygen solution (SOS) infusion.

In FIG. 1C, the guidewire 30 has a thinner proximal end 30' which connects to a thicker resistance end of the guidewire 30". The annular space 18 is defined between the thicker end 30" and the tubular housing 12.

As an example, an oxygen-supersaturated water, including in the form of a physiologic solution such as 5 g % dextrose in water was prepared. After transient hydrostatic compression to approximately 10,000 psi, the solution was infused into an annular space between a 0.016" guidewire and the central channel (i.d.=approximately 0.020") of a conventional coronary angioplasty balloon catheter. No bubbles were formed in the effluent when it was delivered into water or blood. The oxygen concentration was approximately 0.1 to 0.2 cc $O_2$/g. No bubbles were formed even when the liquid was delivered at pressures as low as 100 psi.

Similarly, when oxygen-supersaturated water, after transient hydrostatic compression to 10,000 psi, was infused through the space between a 0.005" to 0.009" guidewire and the core of a hollow polyimide tubing (0.0126" i.d.), no cavitation nucleation was noted in the effluent under water at a similar oxygen concentration and hydrostatic compression.

When a metal wire/tube combination, having a space between of approximately 0.001", was used to deliver oxygen-supersaturated water with a concentration as high as 2 cc $O_2$/g into aqueous media, no bubbles were noted in the effluent when the fluid was delivered at a hydrostatic pressure of 1000 to 10,000 psi after transient compression to 1 kbar.

The advantages of the use of an annular capillary space for stabilizing gas-supersaturated liquids include the ease of fabrication and the ability to use the central channel for other purposes, such as co-axial placement of a guidewire. Wires and various types of tubings, including metal, such as stainless steel; polymeric, such as polyimide and polyethylene terephthalate; and glass, each having dimensional tolerances of a few microns, can be obtained commercially without difficulty. Thus, by inserting a tube or wire within another tube of the same or different type of material, a target dimension of the space between the two can be achieved easily with great precision. The process can be repeated numerous times, so that the overall flow rate can be readily increased to a desired level.

A single such space, created by the use of a guidewire and tube, would allow adequate flow for a coronary artery application. In that environment, it would be desirable to deliver approximately 2 to 10 cc of oxygen per minute. As shown in FIG. 1, perfusion of oxygen-supersaturated physiologic solutions could be performed either between a guidewire 30 and the central channel of a conventional balloon angioplasty catheter or between a guidewire 30 and a thin-walled tubing 12, the outer diameter of which is sufficiently small to allow its passage through the central channel of commercially available coronary angioplasty catheters. The space between the central channel and outer surface of the tube enclosing the guidewire could then be used for other purposes, such as flushing ordinary physiologic crystalloid solutions.

The physiologic solutions include balanced salt solutions, such as those which contain calcium, sodium, magnesium, potassium, and mixtures thereof. It will also be appreciated that suitable physiologic solutions may include buffers selected from a group consisting of phosphates, bicarbonates, and mixtures thereof. Additionally, the physiologic solution may comprise a physiologically balanced salt solution and an oncotic agent selected from the group consisting of albumen, hydroxyethyl starch, and mixtures thereof. It may also be helpful to provide a physiologic solution including a balanced salt solution and a perfluoro chemical, for example. A commercially available solution is known as Fluosol-DA-20%, available from Alpha Therapeutic (Los Angeles, Calif.). It will be readily apparent that other equivalent substituents may be selected, but for brevity they are not specifically enumerated here.

In contrast with conventional angioplasty, the "perfusion wire" 30 for delivery of oxygen-supersaturated aqueous solutions may be used with virtually any clinically available over-the-wire balloon angioplasty system, at a relatively low cost. The rate of infusion could be adjusted to provide any level of needed oxygen delivery. For simplicity, not included in the figures are additional components of the system, such as valves, pressure gauges, controls for maintaining the desired levels of both gas and hydrostatic pressures, automatic cutoff mechanisms activated by a sudden excessive increase in flow velocity or decrease in pressure as a result of fracture of the delivery tubes, a heat exchanger to increase the temperature of the liquid to physiologic levels (37° C.) and a bubble detector (either ultrasonic such as a pulsed Doppler wire, fiberoptic-based reflectance 66 (FIG. 6), or external microphone).

Perfusion of non-gas-supersaturated crystalloids through the central channel of the angioplasty balloon (or an additional hollow tubing incorporated within the perfusion wire) may be used to flush stagnant regions of potential cavitation nucleation beyond the inflated balloon, particularly proximal to the site of infusion of SOS (supersaturated oxygen solutions), during SOS infusion.

In one modification of the OSPS perfusion guidewire design (FIG. 6), the distal end of the hollow tubing contains a section with multiple perforations or exit ports 22. The latter can be made in the wall of the metal tubing or the spring section can be covered with a tubular film (e.g., polyimide, heat shrink polyethylene terephthalate, etc, which can have perforations on the order of 25 to 100 microns in size which are made either with a laser or electron beam or mechanically). In the latter case, the coils of the spring can be spread apart sufficiently to allow access of the oxygen-supersaturated fluid to the holes in the perforated tube.

The perforations are provided for two principal reasons: 1) to improve the uniformity of the perfusion along the axis of the guidewire, and 2) to reduce the mean velocity of flow as a result of the relatively large area available for perfusion (from the sum total of the areas of the perforations) compared to the use of a single annular space. The more uniform, lower flow velocity, for a given flow rate, achieved with this approach results in less turbulence and a reduction in the tendency for gas-supersaturated fluids to generate or grow gas nuclei within vortices in the region into which the gas-supersaturated fluid is delivered.

For applications of stabilized gas-supersaturated liquids requiring high flow rates, the "onionskin" geometry of multiple layers of co-axial tubings 16 is employed at the distal end of the delivery system, as shown in FIGS. 3A and 3B.

The scope of the present invention is not limited to the medical environment. Other applications are manifest in, for instance, fire fighting. If a high flow rate of approximately 2400 liters/minute is used in firefighting, 0.5 to 1 cc/g of inert gas such as nitrogen or carbon dioxide could be stabilized during delivery by the use of approximately 40 to 80 concentric metal tubes, approximately 1 inch in length or shorter, having a space of 30 to 100 microns between tubes, at the distal end of the delivery system. The outer diameter of the housing for the concentric tubes would be similar to currently used nozzles (on the order of 2 inches or less) in firefighting equipment.

Membrane Oxygenation

As another aspect of the present invention, as shown in FIG. 2, I have found that one method of introducing gas at a high partial pressure into a liquid is to use a membrane oxygenator 26 under high pressure. Also depicted is a Parr reactor (30–1500 psi) with an with an impeller stirrer 28. Connected to the stirrer 28 is an air-driven water pump 40 which, in turn, is connected to a high pressure vessel (0.1–1.0 kbar) 34. The oxygen-supersaturated physiologic solution (OSPS) then passes through a fluid regulator and a 0.2 micron filter 68 and a heat exchanger 70 before passage to the OS perfusion guidewire at an approximate pressure of 200–2000 psi. In a preferred membrane oxygenator 26, silicon membranes having a thickness of 75 to 150 microns, are typically used in commercially available membrane oxygenators. At 1 bar, the efficiency of transfer of oxygen is on the order of 200 to 400 cc $O_2$/minute/$m^2$ surface area of silicone membrane.

A prototype membrane oxygenator, for use at a high partial pressure of gas was made by enclosing 5 silicone tubings, each 4 feet long and having an internal diameter of 0.012" and an outer diameter of 0.025", within a 4 ft. long high pressure stainless steel tube. Epoxy was used to seal the space between the tubes over the last several centimeters of the proximal and distal ends of the metal tube. A single fused silica tubing, 0.15 mm i.d./0.25 mm o.d. in size, passed through the proximal seal into the midportion of the metal tubing. It allowed gas to be introduced into the space between the silicon tubings. The inner lumen of the silicone tubings was used for flow of water or 5 g % dextrose in water which had been transiently pressurized to 10,000 psi to eliminate cavitation nuclei. In order to provide an identical pressure of oxygen gas to the outside of the silicon tubings and hydrostatic pressure to the water flowing inside the tubings, a single pressure source-a gas cylinder of compressed oxygen-was used for both. Oxygen from the gas cylinder was delivered directly to the outside of the silicon tubings, and water was delivered to the lumena of the silicone tubings from a high pressure vessel which was pressurized with oxygen from the same gas cylinder.

Since the pressures exerted across the wall of the silicone tubings were identical, the integrity of the tubings was not compromised by the use of pressures in the 100 psi to 1000 psi range. The flow rate of water through the tubings was governed by the resistance of capillary tubings connected distal to the membrane oxygenator.

The oxygen concentration of the effluent from the capillary tubings was what one would predict by the level of oxygen partial pressure used in the membrane oxygenator. Thus, at a partial pressure of 500 psi, approximately 1 cc $O_2$/g water was produced. In addition, because cavitation nuclei had been removed by high hydrostatic compression prior to perfusion through the membrane oxygenator, the effluent delivered from the capillary tubes (typically 25 to 100 microns in internal diameter) into water was free of bubbles.

In the absence of cavitation nuclei in the water perfusing the oxygenator, oxygen could diffuse at a high partial pressure across the wall of the semipermeable membrane or tubings (such as those fabricated from silicone, Teflon, or polypropylene) without creation or growth of gas nuclei in the water. The limited surface area of a prototype high pressure membrane oxygenator permitted fully oxygenated water to be delivered at high gas pressures with a maximum water flow rate of approximately 7 g/minute. Higher flow rates of water, wherein the partial pressure of the gas in the water approximates that in the gas phase, can be achieved by proportionately increasing the surface area of the membrane across which the gas diffuses.

High Pressure Membrane Oxygenation

A high pressure membrane oxygenator 26 (FIG. 2) could be used to fill a large high pressure vessel 34 with water at a desired partial pressure of gas. For example, if a stainless steel gas cylinder (such as a 27 liter cylinder fabricated by Norris) is pressurized with oxygen to 500 psi and a physiologic solution is perfused through a high pressure membrane oxygenator at 600 psi (both gas and hydrostatic pressure), the gas-enriched liquid will flow into the cylinder.

Alternatively, gas can be introduced into cavitation-free liquid through the high pressure membrane oxygenator en route to capillary tubings (including concentric spaces) at the distal end of the delivery system or en route to a high pressure pump. If the membrane oxygenator is designed such that the flow rate of liquid through the oxygenator exceeds its capacity to fully saturate the liquid at the high partial pressure of the gas, the higher hydrostatic pressure of the liquid, compared to the partial pressure of gas dissolved in the liquid, helps to inhibit the formation or growth of cavitation nuclei and bubbles.

In either case, the use of a high pressure membrane oxygenator facilitates the continuous production of gas-supersaturated liquids which do not produce cavitation nucleation at the exit port of the delivery system.

Further Examples

As another example, after application of 0.7 to 1.0 kbar hydrostatic pressure to water which had been equilibrated with oxygen at partial pressures as great as 2,000 psi, no cavitation in the effluent was noted when it was ejected through capillary channels of appropriately small dimensions and made of appropriate materials.

An inverse relationship was found between the maximum oxygen concentration which could be used without bubble formation in the effluent and the size of the silica capillary channels. A 100 micron (i.d.) silica channel will allow ejection of OSPS containing a maximum concentration of 1.5 cc $O_2$/g, while a 5 micron channel will permit a maximum concentration of approximately 4.0 cc $O_2$/g, which corresponds well to the maximum concentration observed by Hemmingsen under static conditions.

As demonstrated both in vitro and in preliminary animal studies in vivo, infusion of OSPS into arterial blood can be used to achieve oxygen partial pressures which can equal and even exceed those achievable at typical pressures used in a hyperbaric oxygen chamber (usually 2.5 bar), without bubble formation. The results are consistent with the observations of Harvey et al, who demonstrated that cavitation in blood under a vacuum from three different species occurs at a mean absolute pressure of 27 mm Hg (i.e., a 0.0355 bar), since blood is a naturally occurring cavitation-free medium.

Other Medical Applications

Thus, tissue ischemia which is currently treated with a hyperbaric oxygen chamber might be treated similarly with a catheter infusion of OSPS. Examples include acute traumatic injuries, unresolved infections, radiation-injured tissue, osteomyelitis, failing skin grafts and flaps, extensive thermal burns, and central nervous system problems.

The lack of pulmonary oxygen toxicity, in contrast to this problem which limits oxygen exposure to usually 90 minutes/day in a hyperbaric chamber, in addition to the potential relative ease of performance and anticipated low cost of implementation, provides an impetus to the use of OSPS as a means for providing local hyperbaric oxygen therapy.

Evidence has accumulated experimentally and clinically that hyperbaric oxygen therapy reduces reperfusion injury, rather than accentuates it, as some investigators anticipated. Hyperbaric oxygen has been found to: (1) inhibit neutrophil adhesion to venules in ischemic tissue; (2) quench lip peroxides with hydroperoxyl radicals which are produced only at oxygen pressures>1 bar; (3) inhibit the conversion of xanthine dehydrogenase to xanthine oxidase; (4) increase tissue levels of superoxide dismutase; (5) greatly improve oxygen diffusion through edematous tissues; and (6) produce marked clinical benefit in a variety of ischemia/reperfusion problems.

In addition to addressing myocardial ischemia during angioplasty, infusion of OSPS may also find utility in reducing reperfusion injury immediately following angioplasty for treatment of acute myocardial infarction. The disclosed OSPS delivery system permits its simultaneous use as a conventional coronary angioplasty guidewire, which would be compatible with commercially available over-the-wire coronary angioplasty catheters. Preliminary in vivo dog coronary artery studies suggest that OSPS infusion through prototype guidewires can be used to reduce myocardial ischemia without adverse effects. Similarly, guidewire-based OSPS infusion could be used to potentially treat a wide variety of other medical conditions associated with regional tissue hypoxia.

In vitro studies demonstrating lack of cavitation inception during OSPS infusion into aqueous media at 1 bar. Turning again to FIG. 2, in order to achieve a target oxygen concentration in 5 g % dextrose in water (D5W), commercially available (Baxter) D5W, after degassing in a vacuum, was rapidly stirred for at least an hour in a 300 cc Parr reactor vessel with an impeller stirrer at 1600 rpm under pressure (500 to 2000 psi) with oxygen from a medical grade oxygen cylinder 38.

In order to eliminate gas nuclei, oxygenated D5W was transferred from the Parr reactor vessel to a high pressure vessel 34 and hydrostatically compressed to 0.2 to 1.0 kbar for at least a few minutes with either an air driven water pump (SC Hydraulics, Inc.) or with a hydraulic compressor 40. The fluid was then delivered through capillary tubings at a hydrostatic pressure which equalled or exceeded the partial pressure of dissolved oxygen to an OSPS perfusion guidewire 30.

The concentration of oxygen achieved was determined by infusion of approximately 1 cc of the fluid from the Parr vessel through a fused silica capillary tubing (i.d. 100 microns or less) into a sealed space within a glass pipette. A 3 mm tip of a titanium probe, mounted at its node point within the pipette and driven with a 300 watt ultrasonic transducer (Sonics and Materials), was used to sonicate the fluid to expel the dissolved gas. Movement of mercury within a graduated column was then used to measure the volume of oxygen released.

Oxygen-supersaturated D5W was injected into water saturated with oxygen at room temperature, and any presence of bubbles in the effluent was detected by argon ion laser induced fluorescence of fluorescein which had been added to the D5W. The absence of bubbles in the effluent was confirmed by 20 ns strobe light microscopy and photon correlation spectroscopy (submicron particle size analyzer).

As noted above, an inverse relationship was discovered between the maximum oxygen concentration achievable in the effluent without cavitation inception and the internal diameter of silica capillary tubing at the distal end of the delivery system. Stability of the effluent was unaffected by temperature<70° C. or by fluid velocities as great as 2,000 cm/sec.

In order to examine blood in vitro for the presence of bubbles during infusion of oxygen-supersaturated D5W, 2-D ultrasound was used to image a 30 cc reservoir. The fluid was delivered at an oxygen concentration of 3 cc O2/g into citrated venous blood, which had been equilibrated with 100% nitrogen, covered with Parafilm, and stirred with a magnetic stirrer, while pO2 was continuously monitored (pO2 electrode, Diamond General). The mean pO2 at which bubbles were first detected was 800 to 900 mm Hg, although pO2's which exceeded the upper range limit for the electrode (2000 mm Hg) were noted before prominent bubble formation in moot runs. When a 0.1 cc aliquot of a sonicated albumin solution, similar to that available commercially as a clinical ultrasound contrast agent, was injected into the reservoir, the reflected echo signal greatly exceeded that noted during OSPS infusion at the threshold pO2.

Preliminary in vivo studies in a dog model of myocardial ischemia during coronary angioplasty. In a dog model of myocardial ischemia during coronary balloon angioplasty, the feasibility of infusion of OSPS through the central channel of a conventional angioplasty balloon catheter was tested in four animals. Under anesthesia with pentobarbital and morphine sulfate and with control of ventilation with a volume respirator, continuous monitoring of ECG and hemodynamics (left ventricular, dp/dt, aortic, pulmonary artery) and intermittent video recording of 2-D ultrasound images of the left ventricle were used to assess the level of myocardial ischemia achieved with 3 minute balloon inflations, with and without infusion of OSPS at 6 to 20 cc/min.

A conventional 3.0 mm coronary angioplasty balloon catheter was advanced into either the circumflex artery or the left anterior descending coronary artery under fluoroscopic control (Precise Optics fluoroscopic unit with a 6" image intensifier and 2:1 optical magnification capability at the output phosphor) through a clinically available guide catheter to perform the balloon inflations. The OSPS was delivered via the central channel of the angioplasty catheter with a prototype perfusion guidewire.

An OSPS with a relatively low concentration of oxygen, 0.1 to 0.2 cc O2/g, in Dulbecco's phosphate buffered saline solution, which contained physiologic concentrations of important ions (sodium, potassium, calcium, magnesium) was used for two reasons. Flow on the order of 10 to 20 cc/min is required to deliver the oxygenated fluid to the myocardium. In addition, OSPS infusion beyond the inflated balloon is likely to completely displace blood. Such concentrations are similar to that achievable in blood in hyperbaric oxygen chambers, and the lack of adverse effects of such therapy on blood is well established. Whether much higher oxygen concentrations, delivered undiluted into the coronary artery, would be associated with adverse effects is unknown by comparison. Baseline coronary blood flow prior to balloon occlusion was estimated to be approximately 50 to 60 cc/min by measurement of flow with a Doppler cuff applied directly to the external surface of the artery in the open chest.

All four dogs demonstrated evidence of a reduction in myocardial ischemia during OSPS infusion and balloon inflation compared to balloon inflation without the infusion. The most salient changes were a reduction in ST segment elevation, a reduction in negative dp/dt, improvement in aortic pulse pressure, and improvement in regional echo wall motion corresponding to the myocardium subtended by the occluded artery. No evidence of bubble formation in the myocardium or in any cardiac chamber was noted by 2-D ultrasound imaging in these dogs. Coronary angiograms demonstrated morphology after the infusion. No pathologic changes were observable by examination of the myocardium and coronary arteries.

I will now describe in additional detail the experimental design and methods by which the invention is practiced.

In Vitro Studies

Figure 5:
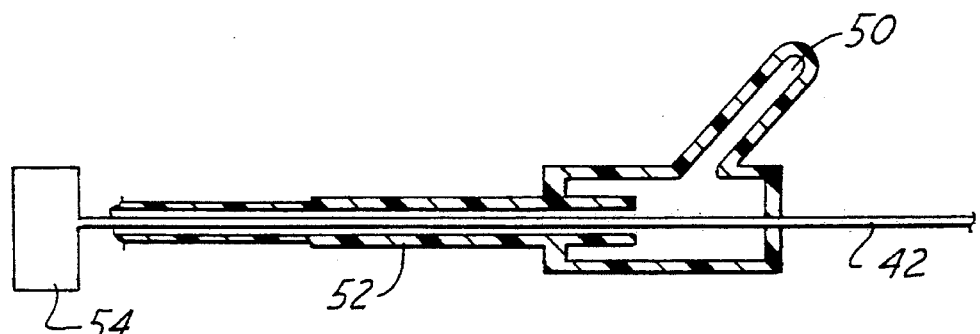
FIG. 5 depicts a proximal end of the perfusion guidewire.
Figure 6:
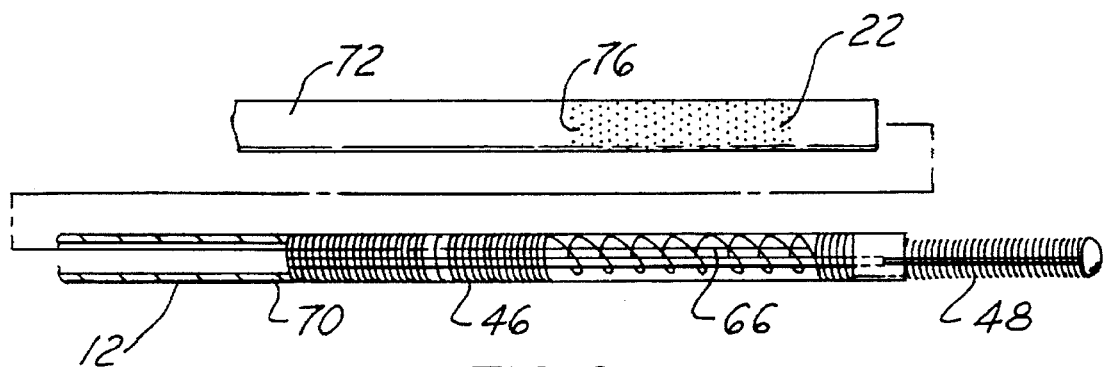
FIG. 6 depicts a distal end of an oxygen-saturated physiological solution perfusion guidewire (alternate embodiment).

Turning now to FIGS. 4–6, there is depicted a fiberoptic 42 within a hollow stainless steel tube 44. A radio-opaque flexible spring 46 is spotwelded to the hollow stainless steel tube 44. At an end of the spring 46 remote from the stainless steel tube 44, there is defined an exit port 22 for oxygen-supersaturated solution delivery. The guidewire 30 extends beyond the first spring 46. At a leading end of the guidewire 30 is another radio-opaque flexible spring section 48 to facilitate location of the delivery system within an environment of interest.

FIG. 5 depicts a proximal end of the perfusion guidewire. OSPS is introduced at OSPS inlet 50. If desired, a proximal end of the hollow stainless steel tubing may be provided with a thicker wall section 52. If desired, the delivery system may include means for providing a laser output 54 coupled to the fiberoptic 42.

The capillary channel for OSPS perfusion consists of the space 18 within a hollow SS (medical grade 304 or 316) guidewire (FIG. 1E) (0.014" o.d., 0.009" to 0.010" i.d.), the distal 15 cm of which has the spring design for flexibility and an inner safety wire (0.003" to 0.005"; spot welded to the spring) which serves to prevent separation of the coils and to reduce the lumen size. Alternatively, a highly flexible, hollow nitinol (titanium/nickel alloy) wire having similar dimensions to the hollow SS wire is spot welded to the latter. In either case, a 3 cm long radio-opaque distal platinum spring (0.014" o.d.) terminates the safety wire which extends beyond the point of infusion.

The advantages of this design include mechanical similarity to and compatibility with currently used angioplasty guidewires and a high pressure rating (1 kbar). Overall capillary channel resistance is designed to permit a flow rate of approximately 20 cc/min. at a hydrostatic pressure of 1,000 to 2,000 psi applied to the proximal end of the perfusion guidewire.

Turning now to FIG. 6, there is depicted an alternate embodiment of the OSPS perfusion guidewire. There is depicted a high pressure tubular housing 12 defining a lumen therewithin. The housing 12 has a distal end 70. A coiled spring 46 extends from the tubular housing 12. A jacket 72 includes a proximal sleeve section and a distal perforated section 76 that defines exit ports 22. The proximal sleeve section is located proximate to the distal end 70 of the tubular housing 12. The proximal sleeve section of the jacket is placed over the coiled spring to prevent leakage of the solution through the coiled spring, while allowing perfusion of the solution through the exit ports of the perforated section. The oxygen-saturated physiologic solution is stabilized upon emergence from the apparatus so that the oxygen is transported to a site of interest in solution in a supersaturated state without associated bubble formation and cavitation proximate the exit ports.

The apparatus may also include one or more fiberoptics 42 located axially within the tubular housing and the coiled spring. The fiberoptics conduct radiant energy and receive reflected energy, and may be used for bubble detection.

The coiled spring 46 includes a section wherein successive coils of the spring are spaced apart to allow the oxygen-saturated physiologic solution to pass through from the exit ports.

A solid plug is inserted within a guidewire spring section 48 to block forward flow of the OSPS.

A potentially important failure mode of an OSPS perfusion guidewire would be the presence of bubbles in the effluent. Therefore, an on-line bubble detector is incorporated in the guidewire. As a simple approach, the output is coupled to the proximal end of a fiberoptic 66, the distal end of which terminates within the OSPS capillary channel near the point of infusion. Light which would be reflected by potential bubbles is monitored via this fiberoptic or via a second fiberoptic. Interference by absorption of light by blood is not problematic, since all blood is replaced or deleted by infusion of translucent crystalloid solutions.

An alternative approach is to use a microscopic ultrasound transducer (approximately 0.001" thick) which is mounted on the safety wire, just proximal to the radio-opaque distal spring assembly. Two lead wires connect the transducer to the power source. Although this source is unaffected by the presence of blood, it is likely to be more costly and perhaps no more reliable in a translucent medium than the fiberoptic approach.

The most important factors affecting the stability of oxygen-supersaturated water, following hydrostatic compression during its infusion into the ambient environment from a high pressure vessel are the oxygen concentration of the effluent and the diameter of the capillary tubing at the exit port. In order to ensure that the capillary channel within the perfusion guidewire is sufficiently small to stabilize OSPS during a coronary infusion, it is designed to stabilize an oxygen concentration which is greater than that to be used in a clinical setting. For example, if a concentration of 0.2 cc O2/g OSPS is used in vivo, the perfusion guidewire would permit bubble-free infusion of the fluid having a concentration of at least 0.4 cc O2/g.

It is possible to deploy non-axisymmetric capillary luminal geometry to achieve the maximum oxygen concentration without cavitation inception during infusion into a 1 bar aqueous environment. Square (glass tubing width—50 microns), rectangular (50×200 micron glass tubing), and annular lumina (the latter resulting from the use of a wire within a circular lumen) have each been used to infuse OSPS with a concentration as high as 2 cc O2/g into aqueous media without bubble formation.

The surface properties of candidate material for fabrication of capillary channels may affect the stability of OSPS during infusion. For example, hydrophobic materials, such as hollow carbon fibers with an i.d. of 5 microns, should not be used to attempt to stabilize OSPS with 2 cc O2/g during its infusion into a 1 bar aqueous environment. Hydrophotic impurities have been implicated as potential sources of cavitation nuclei. A hydrophilic surface in contact with OSPS is preferred.

While the best modes for carrying out the invention have been described in detail, those familiar with the art to which this invention relates will recognize various alternative designs and embodiments for practicing the invention as defined by the following claims.

What is claimed is:

1. An apparatus for intra-arterial delivery of an oxygen-saturated solution during angioplasty, the oxygen-saturated solution being stabilized upon emergence from the apparatus without associated cavitation comprising:

a high pressure tubular housing defining a lumen therewithin, the housing having a distal end;

a coiled spring extending from the tubular housing;

a jacket including a proximal sleeve section and a distal perforated section that defines exit ports, the proximal sleeve section being located proximate to the distal end of the tubular housing, the proximal sleeve section of the jacket being placed over the coiled spring to prevent leakage of the solution through the coiled spring, while allowing perfusion of the solution through the exit ports of the perforated section, the exit ports being sized to allow the solution to be delivered so that the solution has a composition characterized by a fluid continuum of uniform density upon emergence from an exit port.

2. The apparatus of claim 1 further comprising:

one or more fiberoptics located axially within the tubular housing and the coiled spring, the one or more fiberoptics transmitting radiant energy and receiving reflected energy.

3. The apparatus of claim 1 wherein the coiled spring includes a section wherein successive coils of the spring are spaced apart to allow the oxygen-saturated solution to pass through from the exit ports.

4. The apparatus of claim 1 further including the oxygen-saturated solution, wherein the solution comprises 5 g % dextrose in water.

5. The apparatus of claim 1 further including the oxygen-saturated solution, wherein the solution comprises a normal saline solution.

6. The apparatus of claim 1 further including the oxygen-saturated solution, wherein the solution comprises a physiologically-balanced salt solution, the salt solution being selected from a group consisting of a solution of calcium, sodium potassium, magnesium, and mixtures thereof.

7. The apparatus of claim 1 further including the oxygen-saturated solution, wherein the solution comprises a buffer selected from the group consisting of a phosphate, a bicarbonate, and mixtures thereof.

8. The apparatus of claim 1 further including the oxygen-saturated solution, wherein the solution comprises a physiologically-balanced salt solution and an oncotic agent selected from the group consisting of albumin, hydroxyethyl starch, and mixtures thereof.

9. The apparatus of claim 1 further including the oxygen-saturated solution, wherein the solution comprises a balanced salt solution and a perfluorochemical.

10. An apparatus for delivering a gas-supersaturated liquid from a source of gas into a site within an environment with a low concentration of the gas in relation to that of the source, comprising:

a high pressure tubular housing defining a lumen therewithin;

a guide wire axially disposed within the lumen, the guide wire and the lumen defining therebetween an annular space, a charge of gas-saturated liquid disposed within the annular space to eliminate gas nuclei therefrom, the charge having a composition characterized by a fluid continuum of uniform density;

the gas-supersaturated liquid emerging from the annular space after passage of the charge, the liquid also being characterized by a fluid continuum of uniform density upon emergence from the annular space so that the gas is transported to a site of interest in a supersaturated state, the gas being liberated therefrom remote from the apparatus without associated bubble formation and cavitation proximate the annular space.

11. The apparatus of claim 10 further comprising:

one or more fiberoptics located axially within the tubular housing, the fiberoptics transmitting radiant energy and receiving reflected energy.

12. The apparatus of claim 10 further comprising a coil spring extending from the tubular housing for flexibility so that the apparatus may navigate safely through tortuous passageways.

13. An apparatus for intra-arterial delivery of an oxygen-saturated solution without bubble formation and cavitation, comprising:

a high pressure tubular housing defining a lumen therewithin, the housing having a distal end;

a coiled spring extending from the tubular housing; and a jacket including a proximal sleeve section and a distal perforated section;

exit ports defined in the distal perforated section, the proximal sleeve section being located proximate to the distal end of the tubular housing, the proximal sleeve section of the jacket being placed over the coiled spring to prevent leakage of the solution to the coiled spring, the exit ports being sized to allow perfusion of the solution through the exit ports, the solution being characterized by a fluid continuum of uniform density upon emergence from the exit ports.

14. An apparatus for delivering a gas-supersaturated liquid from a source of gas into a site within an environment with a low concentration of the gas in relation to that of the source comprising:

a high pressure tubular housing defining a lumen therewithin;

a guide wire axially disposed within the lumen, the guide wire and the lumen defining therebetween an annular space; and the annular space being sized to allow the gas-supersaturated liquid to emerge from the annular space, wherein the liquid is characterized by a fluid continuum of uniform density upon emergence from the annular space.

* * * * *